United States Patent
Kamihara et al.

(10) Patent No.: US 6,552,197 B2
(45) Date of Patent: Apr. 22, 2003

(54) CONDENSED-HEXACYCLIC COMPOUNDS AND A PROCESS THEREFOR

(75) Inventors: Shinji Kamihara, Tokyo (JP); Kazuaki Kanai, Tokyo (JP); Shigeru Noguchi, Tokyo (JP); Hirofumi Terasawa, Tokyo (JP); Hiroaki Kitaoka, Tokyo (JP)

(73) Assignees: Daiichi Pharmaceutical Co., Ltd., Tokyo (JP); Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/876,945

(22) Filed: Jun. 11, 2001

(65) Prior Publication Data

US 2001/0034446 A1 Oct. 25, 2001

Related U.S. Application Data

(62) Division of application No. 08/501,933, filed on Jul. 13, 1995.

(30) Foreign Application Priority Data

Apr. 10, 1995 (JP) .............................................. 7-083717

(51) Int. Cl.$^7$ ............................................ C07D 471/00
(52) U.S. Cl. ........................................ 546/46; 546/48
(58) Field of Search ...................................... 546/46, 48

(56) References Cited

U.S. PATENT DOCUMENTS

| 4,939,255 A | | 7/1990 | Tagawa et al. | ................ 546/48 |
| 5,061,795 A | | 10/1991 | Tagawa et al. | ................ 546/48 |
| 5,637,770 A | * | 6/1997 | Terasawa et al. | ............ 546/211 |

FOREIGN PATENT DOCUMENTS

| EP | 0 296 597 | 12/1988 |
| EP | 0 495 432 | 7/1992 |
| JP | 6-87746 | 3/1994 |

OTHER PUBLICATIONS

Mitsui et al. (Jpn. J. Cancer Res. (1995), 86(8), 776–782) Abstract.*
Mitsui et al, 84$^{th}$ Annual Meeting of the American Association of Cancer Research Poster No. 2510 Figures 1–3 (1993).

* cited by examiner

*Primary Examiner*—Bruck Kifle
(74) *Attorney, Agent, or Firm*—Oblon, Spivak, McClelland, Maier & Neustadt, P.C.

(57) ABSTRACT

Disclosed are a process for the preparation of a compound represented by the formula (1), which comprises treating a compound represented by the formula (2) with methanesulfonic acid and then subjecting the thus-treated compound to recrystallization; and Compound (1) so obtained.

This Compound (1) is free of hygroscopicity, excellent in filterability and solubility and easy in handling. Furthermore, according to the preparation process of the present invention, an unnecessary isomer can be converted into the target one and separation of the target isomer can be conducted easily.

7 Claims, 1 Drawing Sheet

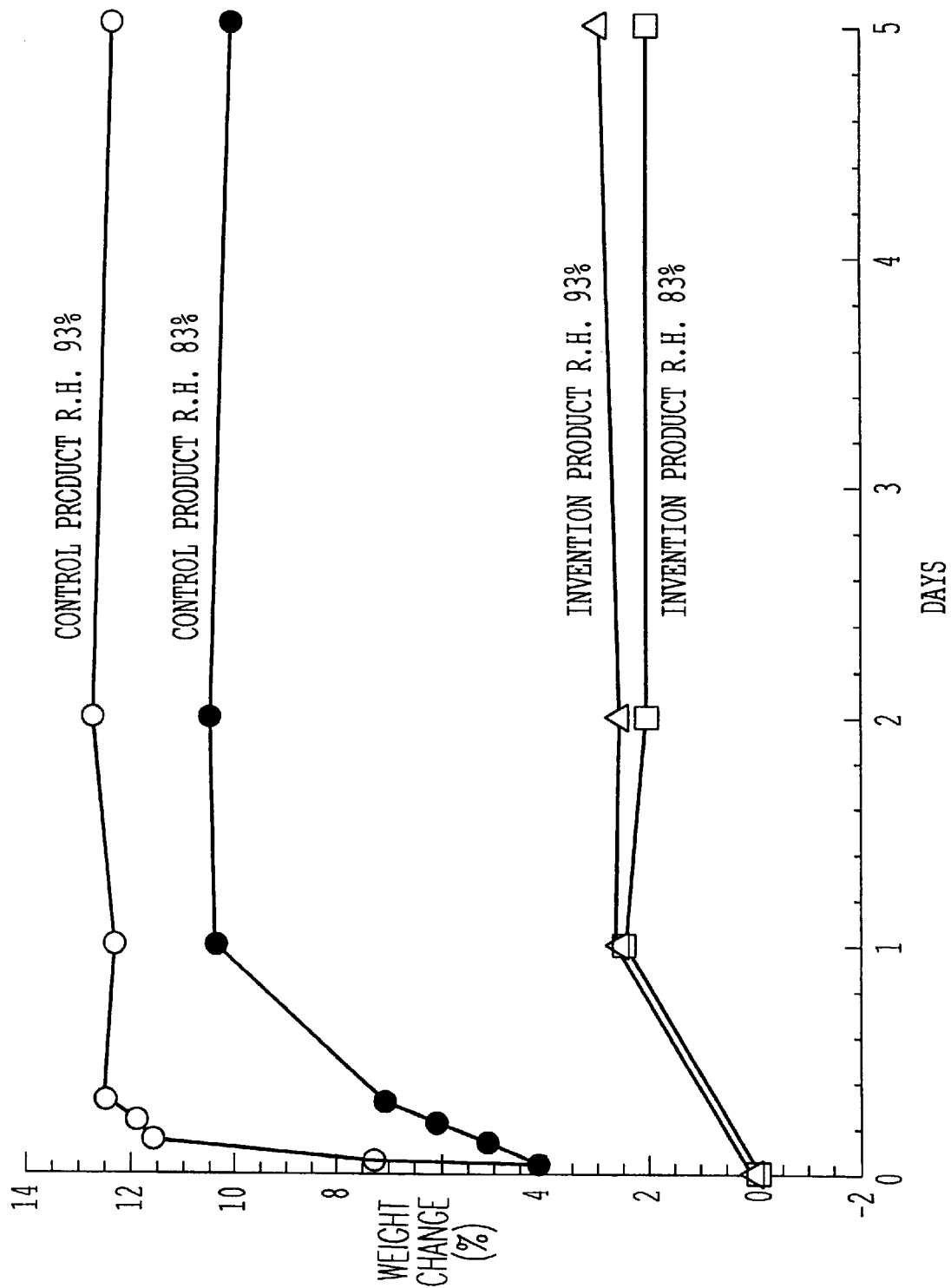

CONDENSED-HEXACYCLIC COMPOUNDS AND A PROCESS THEREFOR

This application is a Division of application Ser. No. 08/501,933 filed on Jul. 13, 1995.

TECHNICAL FIELD

This invention relates to a camptothecin derivative having antitumor activities and an industrially advantageous preparation process therefor.

BACKGROUND ART

The compound represented by the following formula (4):

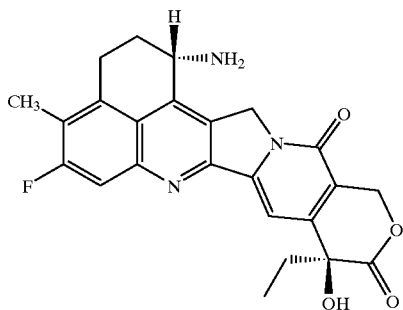

(4)

that is, [(1S,9S)-1-amino-9-ethyl-5-fluoro-2,3-dihydro-9-hydroxy-4-methyl-1H,12H-benzo[de]pyrano[3',4':6,7]-indolizino[1,2-b]quinoline-10,13(9H,15H)-dione] or a salt thereof is a camptothecin derivative which exhibits excellent antitumor activities (Japanese Patent Laid-Open No. 87746/1994).

The conventional hydrochloride, sulfate, hydrobromide, nitrate or the like of the above compound are, however, accompanied by one or more disadvantages such as high hygroscopicity, low filterability and/or low solubility, leading to intractable handling property at industrial preparation.

Further, in order to convert any one of these inorganic salts into a pharmacologically-useful acid addition salt such as the tartrate, malonate or malate, it requires the conversion of the inorganic salt into the sparingly-soluble free compound prior to the formation of the desired salt. Such conventional salts thus require the extra step and in addition, the free compound had low solubility and cannot be handled easily. These conventional salts are therefore disadvantageous from the industrial viewpoint.

Upon preparation of Compound (4) according to the conventional procedure, an unnecessary stereoisomer is formed together with the target stereoisomer theoretically in equal amounts, lowering the yield of the desired compound. And further, to obtain the target stereoisomer, high-performance liquid chromatography should be used. So the target stereoisomer cannot be prepared advantageously in industry by the conventional preparation procedure.

An object of the present invention is therefore to provide a novel acid addition salt of a camptothecin derivative, said salt being free of hygroscopicity, having excellent filterability and solubility and being pharmacologically useful; and also an industrially advantageous preparation process therefor.

With the foregoing in view, the present inventors have conducted with an extensive investigation. As a result, it has been found that treatment of the compound represented by the below-described formula (2) with methanesulfonic acid allows isomerization upon removal of the amino-protecting group proceed so that the target isomer can be obtained in an improved yield; that the repetition of the above reaction makes it possible to convert an unnecessary isomer, which has remained after the separation of the necessary isomer, into the desired isomer; that the target product can be selectively collected easily by recrystallization while making use of the difference in solubility between the unnecessary isomer and the desired isomer; and that the methanesulfonate as the target product is useful as a pharmaceutical for the lack of hygroscopicity and good filterability and solubility, leading to the completion of the present invention.

DISCLOSURE OF THE INVENTION

The present invention therefore provides the methanesulfonate of a camptothecin derivative, said methanesulfonate being represented by the following formula (1):

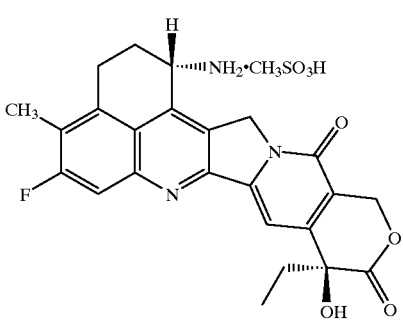

(1)

or a hydrate thereof, and also a preparation process therefor.

The present invention also provides a pharmaceutical composition comprising the Compound (1) or a pharmaceutically-acceptable salt thereof.

BRIEF DESCRIPTION OF THE DRAWINGS

FIG. 1 diagrammatically illustrates weight changes of an invention compound and a control product due to moisture absorption.

BEST MODES FOR CARRYING OUT THE INVENTION

The methanesulfonate represented by the formula (1) or a hydrate thereof is in the form of crystals which are free of hygroscopicity, have excellent filterability and solubility and can be easily processed or handled. As the hydrate, the dihydrate of the methanesulfonate is preferred.

The methanesulfonate (1) of the present invention can be prepared, for example, in accordance with the following reaction scheme.

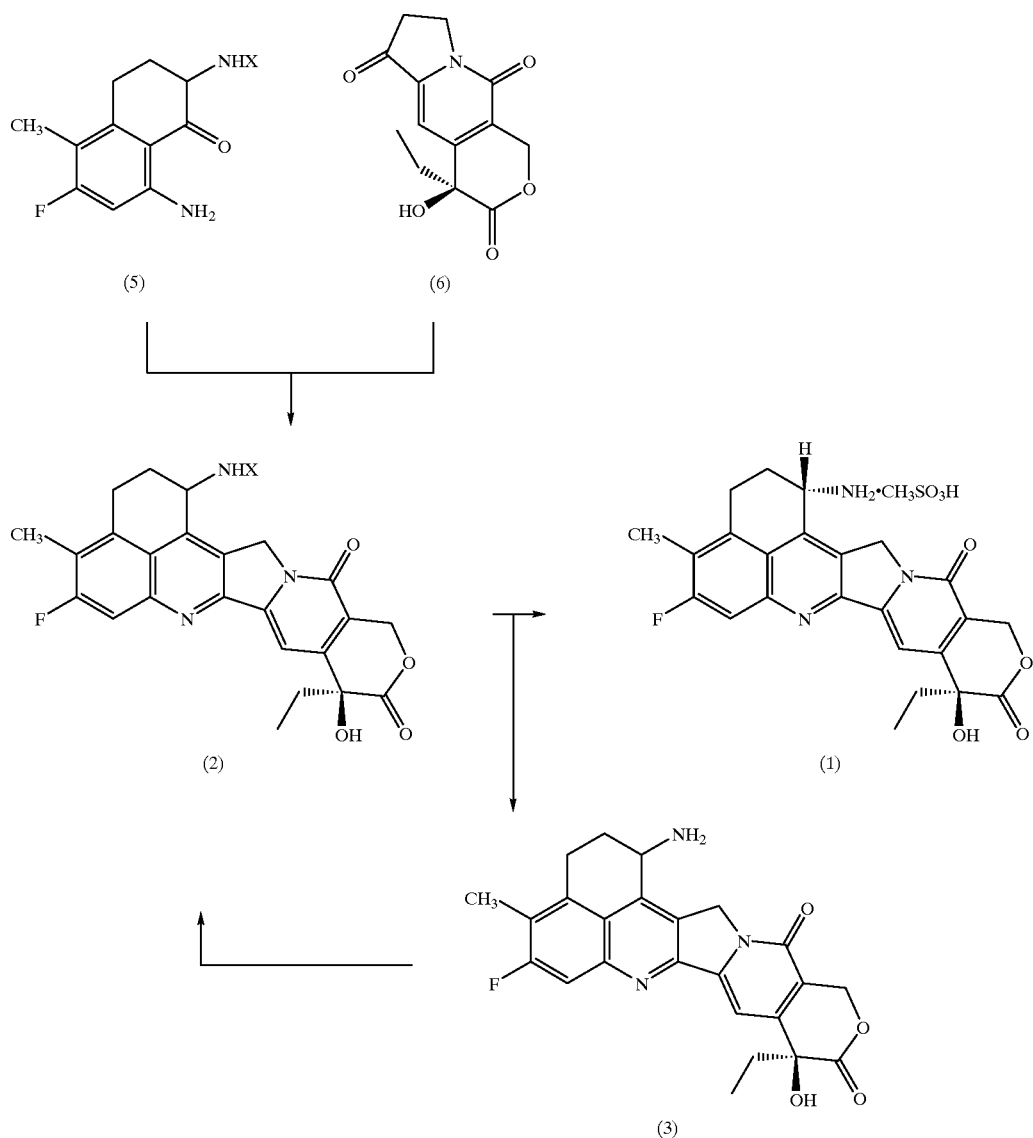

wherein X represents a protecting group removable by methanesulfonic acid.

Described specifically, the methanesulfonate of the camptothecin derivative, said methanesulfonate being represented by the formula (1), or a hydrate thereof can be obtained by reacting Compound (5) with Compound (6) by a known procedure (Japanese Patent Laid-Open No. 87746/1994) to yield Compound (2), treating Compound (2) with methanesulfonic acid and then subjecting the resulting compound to recrystallization.

The methanesulfonate (1) or its hydrate of the present invention can also be obtained by protecting the amino group of the compound represented by the formula (3) with a protecting group removable by methanesulfonic acid, preferably with an acetyl group, treating the compound with methanesulfonic acid and then subjecting the resulting compound to recrystallization. Even if Compound (3) obtained above is derived from the unnecessary isomer which has remained after separation of Compound (1), it can be converted into Compound (1), so it is still useful.

Preparation processes for these compounds will hereinafter be described specifically.

Compound (2) can be obtained by reacting Compound (5) with Compound (6) by a known procedure (the process disclosed in Japanese Patent Laid-Open No. 87746/1994 or the like). In Compound (2), the carbon atom to which the protected amino group is bonded is an asymmetric carbon atom. Compound (2) is generally obtained as a mixture of two isomers, one being an S-form and the other an R-form in the configuration of the protected amino group on the asymmetric carbon atom.

The methanesulfonate (1) or its hydrate of the present invention can be obtained by treating Compound (2) with methanesulfonic acid and then subjecting the resulting compound to recrystallization.

As for the amino-protecting group in Compound (2), it is preferred to employ a group removable by the subsequent treatment with methanesulfonic acid. Examples of such a protecting group include acyl groups such as alkanoyl and benzoyl groups which may be substituted by one or more halogen atoms, e.g., acetyl, chloroacetyl, trichloroacetyl and trifluoroacetyl; alkoxycarbonyl groups such as tert-butyloxycarbonyl; alkanoyloxymethyl groups such as pivaroyloxymethyl; a tetrahydropyranyl group; and a formyl group. Among these, acyl groups are preferred, with $C_{2-6}$ alkanoyl groups, which may be substituted by one or more halogen atoms, being more preferred. An acetyl group is particularly preferred from the viewpoints of the cost and the ease of handling.

The treatment with methanesulfonic acid is conducted not only for the deprotection of Compound (2) but also for the formation of a salt which is free of hygroscopicity, excellent in filterability and solubility, and stable and therefore easily handled, and for the conversion into the desired isomer.

Upon deprotection and salt-forming reaction, it is preferred to use methanesulfonic acid in an amount ranging from 5 times to 30 times based on the weight of Compound (2) [volume/weight: the ratio will be designated as 1 times when methanesulfonic acid is used in an amount of 1 ml relative to 1 g of Compound (2)], and about 15 times being particularly preferred (When methanesulfonic acid is used on a weight basis, the amount to be used can be calculated by multiplying its volume by its specific gravity, that is, about 1.5).

Upon treatment with methanesulfonic acid, it is convenient to use the acid in the form of an aqueous solution. The aqueous solution of methanesulfonic acid is preferred to have a concentration in a range of from 10% to 60%, more preferably about 30%.

The treatment with methanesulfonic acid may be conducted with an aqueous methanesulfonic acid solution only or in the presence of an organic solvent. Examples of such a solvent include aromatic solvents such as toluene and xylene, alcoholic solvents such as methanol, ethanol and isopropanol, and ether solvents such as dioxane and tetrahydrofuran. When an organic solvent is employed, it is preferred to use the solvent in a range up to about twice as much as the volume of the aqueous methanesulfonic acid solution.

The treatment may be conducted in a temperature range of from room temperature to the reflux temperature of the solvent employed. A temperature range of from 100° C. to 120° C. is preferred.

For the treatment, one hour to several days may be necessary. In general, the treatment for 7 hours or so under stirring is enough for the complete deprotection.

The above-described treatment conducted using methanesulfonic acid yields a stereoisomer mixture which contains the stereoisomer of the present invention having the desired steric configuration and the unnecessary stereoisomer at a ratio of approximately 1:1. Each of the deprotected compounds is in the form of the methanesulfonate and is dissolved in the aqueous layer. A solid mixture can therefore be obtained by removing water from the aqueous layer.

The solid isomer mixture so obtained is then recrystallized from a water-alcohol mixture, for example, a mixed solvent of water and an alcoholic solvent such as methanol, ethanol or isopropanol. This surprisingly results in the selective preparation of Compound (1), that is, the methanesulfonate of Compound (4) having S-configurations at the 1-amino group and the 9-position—said Compound (4) being the compound having the target steric configuration from Compound (3). The methanesulfonate of the isomer having the target configuration can be obtained as crystals because its solubility is lower than unnecessary isomer. Thus, the target compound can be selectively collected with ease. The stereoisomer having the unnecessary configuration can hence be obtained in the form of a solution in the recrystallization mother liquid.

Incidentally, to obtain a purer target isomer, recrystallization may be repeated for several times.

The unnecessary stereoisomer within Compound (3), which remains in the recrystallization mother liquid, can be converted into Compound (1) of the target configuration according to the following procedure. Described specifically, a protecting group is introduced into the 1-amino group of the unnecessary stereoisomer, for instance, the compound having an R-configuration around the 1-amino group and an S-configuration at the 9-position, followed by deprotection reaction, whereby concurrently with deprotection, isomerization proceeds on the carbon atom to which the amino group is bonded. The introduction of the protecting group and deprotection reaction thereof are conducted under similar conditions as those described above. By repeating this series of reactions, most of Compounds (3) and Compounds (2) can be converted into Compound (1).

The process according to the present invention can also be applied as a process to obtain Compounds (A) and (C) as is shown in the following reaction scheme.

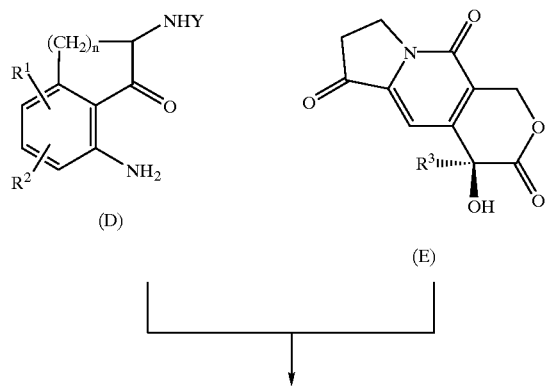

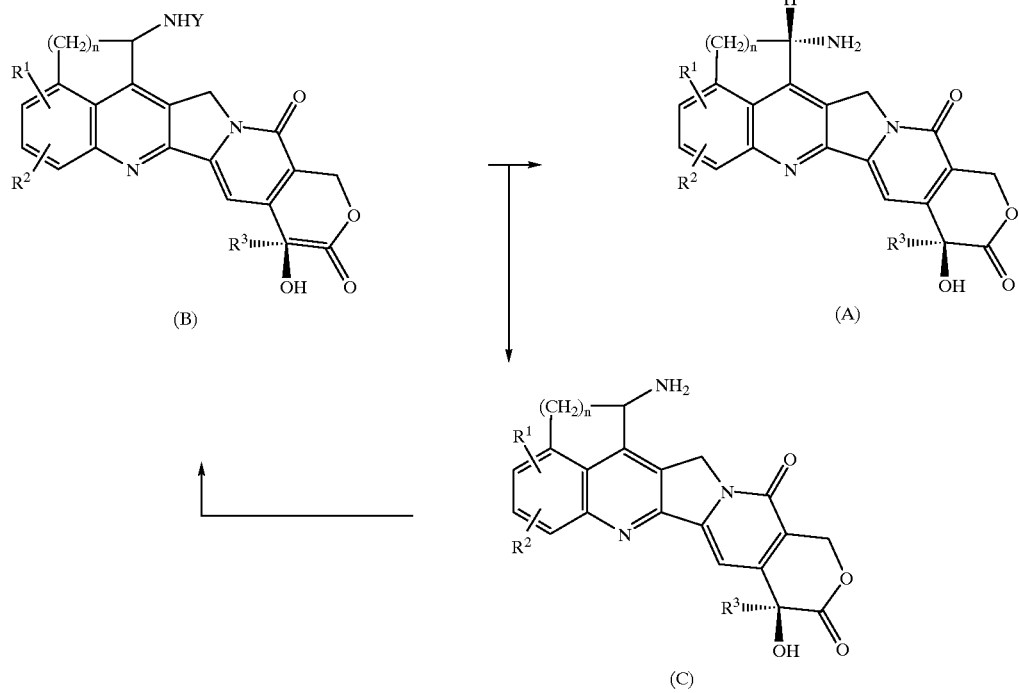

(B)

(A)

(C)

wherein $R^1$ and $R^2$ each independently represents a hydrogen atom, a halogen atom, a hydroxyl group or a $C_{1-6}$ alkyl group, $R^3$ represents a $C_{1-6}$ alkyl group, Y represents a protecting group removable by an acid, and n stands for an integer of 1–3.

Compound (A) can be obtained by reacting Compound (D) with Compound (E) in a known manner (Japanese Patent Laid-Open No. 87746/1994) to obtain Compound (B), treating the resulting Compound (B) in the presence of an acid and then subjecting the thus-treated compound to recrystallization. Compound (A) can also be obtained by protecting the amino group in Compound (C) with a substituent removable by an acid, treating the protected compound with an acid and then subjecting the resulting compound to recrystallization.

This process can of course be applied as a process for selectively preparing an isomer of Compound (A) having an S configuration at the position of the substituent "—NHY", or a salt thereof by treating an isomer mixture of Compound (B) containing abundantly an isomer having an R configuration around the "—NHY" position, in the presence of an acid and then subjecting the resulting mixture to recrystallization.

The methanesulfonate (1) of the camptothecin derivative or the hydrate thereof according to the present invention is free of hygroscopicity, excellent in filterability and solubility and advantageous in handling so that it is useful as a pharmaceutical, particularly as an antitumor agent. When this methanesulfonate (1) of the camptothecin derivative or the hydrate thereof is used as a pharmaceutical, it is desired to use it in the form of a pharmaceutical composition composed of the compound and a pharmaceutically acceptable carrier.

The preparation process according to the present invention is industrially advantageous, because the target compound can be selectively collected with ease by converting an unnecessary isomer into the target isomer through methanesulfonic acid treatment and then subjecting the so-obtained isomer to recrystallization.

The present invention will hereinafter be described more specifically by Examples. It should however be borne in mind that the present invention is not limited to or by the following Examples.

REFERENTIAL EXAMPLE 1

(4S)-4-Ethyl-7,8-dihydro-4-hydroxy-1H-pyrano[3,4-f] indolizine-3,6,10(4H)-trione To 90 ml of 90% trifluoroacetic acid, 3.5 g of (4S)-4-ethyl-6,6-(ethylenedioxy)-7,8-dihydro-4-hydroxy-1H-pyrano[3,4-f]indolizine-3,10(4H)-dione were added at room temperature over 5 minutes, followed by stirring at the same temperature for 30 minutes. After completion of the reaction, the solvent was removed under reduced pressure, followed by the thorough removal of the solvent by a vacuum pump. To the residue so obtained was added 20 ml of ethyl acetate. The crystals precipitated were collected by filtration, whereby 2.4 g of the title compound were obtained.

REFERENTIAL EXAMPLE 2

(9S)-1-Acetylamino-9-ethyl-5-fluoro-2,3-dihydro-9-hydroxy-4-methyl-1H,12H-benzo[de]pyrano[3',4':6,7]-indolizino[1,2-b]quinoline-10,13(9H,15H)-dione To 150 mg of 2-acetylamino-8-amino-6-fluoro-5-methyl-1-tetralone and 158 mg of (4S)-4-ethyl-7,8-dihydro-4-hydroxy-1H-pyrano[3,4-f]indolizine-3,6,10(4H)-trione, 30 ml of toluene and then 150 mg of pyridinium p-toluenesulfonate were added, followed by heating at an external temperature of 120° C. under reflux for 28 hours. After completion of the reaction, the solvent was removed under reduced pressure. Acetone was added to the residue and crystals so precipitated were collected by filtration, whereby 169 mg of the title compound were obtained. Melting point: 225–235° C. (decomposed)

$^1$H—NMR(CDCl$_3$)δ:
1.05(3H,t,J=7.4 Hz), 1.88(2H,q,J=7.4 Hz), 2.15(3H,s), 2.19-2.43(2H,m), 2.44(3H,s), 3.12-3.17(2H,m), 3.72 (1H,s), 5.15-5.33(3H,m), 5.58-5.72(2H,m), 5.98(1H, br-s), 7.57(1H,s), 7.67(1H,d,J=10.9 Hz).

REFERENTIAL EXAMPLE 3

(9S)-1-Acetylamino-9-ethyl-5-fluoro-2,3-dihydro-9-hydroxy-4-methyl-1H,12H-benzo[de]pyrano[3',4':6,7]-indolizino[1,2-b]quinoline-10,13(9H,15H)-dione To 2.00 g of 2-acetylamino-8-amino-6-fluoro-5-methyl-1-tetralone and 2.10 g of (4S)-4-ethyl-7,8-dihydro-4-hydroxy-1H-pyrano[3,4-f]indolizine-3,6,10(4H)-trione, 250 ml of toluene and then 0.1 g of pyridinium p-toluenesulfonate were added, followed by heating under reflux for 3 hours. The mixture was added with 0.1 g of pyridinium p-toluenesulfonate, followed by heating under reflux for 2.5 hours. The mixture was then added with 0.1 g of pyridinium p-toluenesulfonate, followed by heating under reflux for 38 hours. The reaction mixture was cooled. The solvent was then removed under reduced pressure. To a crystalline residue, acetone was added and the crystals so precipitated were collected by filtration, whereby 3.48 g of the title compound were obtained. Melting point: 225-235° C. (decomposed)

$^1$H—NMR (CDCl$_3$)δ:
1.05(3H,t,J=7.4 Hz), 1.88(2H,q,J=7.4 Hz), 2.15(3H,s), 2.19-2.43(2H,m), 2.44(3H,s), 3.12-3.17(2H,m), 3.72 (1H,s), 5.15-5.33(2H,m), 5.58-5.72(2H,m), 5.98(1H, br-s), 7.57(1H,s), 7.67(10H,d,J=10.9 Hz).

EXAMPLE 1

(1S,9S)-1-Amino-9-ethyl-5-fluoro-2,3-dihydro-9-hydroxy-4-methyl-1H,12H-benzo[de]pyrano[3',4':6,7]-indolizino[1,2-b]quinoline-10,13(9H,15H)-dione•methanesulfonate•dihydrate To 5.0 g of (9S)-1-acetylamino-9-ethyl-5-fluoro-2,3-dihydro-9-hydroxy-4-methyl-1H,12H-benzo[de]pyrano-[3',4':6,7]indolizino[1,2-b]quinoline-10,13(9H,15H)-dione, 150 ml of water were added. To the resulting mixture, 75 ml of methanesulfonic acid and then 150 ml of toluene were added, followed by heating under reflux for 6.5 hours. The reaction mixture was cooled down and the aqueous layer was collected by a separatory funnel. The aqueous layer so collected was filtered through a glass filter. The solvent was removed from the filtrate. To the residue so obtained, 300 ml of methanol and then 200 ml of ethanol were added. The resulting mixture was thereafter cooled. The crystals so precipitated were collected by filtration and washed with ethanol, whereby 2.6 g of crude crystals were obtained together with the mother liquor.

The crude crystals so obtained were stirred in a slurry in methanol to yield 2.2 g of the crude crystals. To the resulting crude crystals, 140 ml of water were added, followed by filtration through a membrane filter. After the addition of ethanol to the crystals, the solvent was removed. A 4:1 mixed solvent (165 ml) of ethanol and water was added to the residue so obtained, followed by heating to dissolve the residue in the solvent. The resulting solution was allowed to stand overnight at room temperature. The crystals precipitated were collected by filtration, followed by washing with ethanol, whereby 1.6 g of the title compound were obtained.

Melting point: 245–255° C. (decomposed)

$^1$H—NMR(D$_2$O)δ:
0.73(3H,t,J=7.3 Hz), 1.75(2H,q,J=7.3 Hz), 2.13(3H,s), 2.50-2.62(2H,m), 2.65(3H,s), 2.83-3.00(1H,m), 3.18-3.30(1H,m), 5.16-5.45(5H,m), 7.06(1H,s), 7.10(1H,d, J=10.6 Hz).

Elementary analysis for C$_{24}$H$_{22}$FN$_3$O$_4$·CH$_3$SO$_3$H·2H$_2$O:

Calculated: C, 52.90; H, 5.33; N, 7.40 (%)

Found: C, 52.74; H, 5.15; N, 7.35 (%)

IR(KBr)cm$^{-1}$:

3409, 2936, 1747, 1658, 1589, 1503, 1420, 1252, 1165, 1112, 1044, 884, 773, 554.

EXAMPLE 2

The mother liquid obtained in Example 1 was concentrated under reduced pressure. To the residue, 200 ml of methanol were added, followed by the dropwise addition of 162 ml of triethylamine under ice cooling. After having been confirmed that the mixture was not acidic, 9.9 ml of acetic anhydride were added at room temperature, followed by stirring at the same temperature for one hour. After completion of the reaction, water was added to the reaction mixture. The crystals precipitated were collected by filtration, washed with water and ethanol, and then dried under reduced pressure, whereby 1.9 g of (9S)-1-acetylamino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione were obtained. The product so obtained was deprotected as in Example 1, whereby (1S,9S)-1-amino-9-ethyl-5-fluoro-2,3-dihydro-9-hydroxy-4-methyl-1H,12H-benzo[de]pyrano[3',4':6,7]indolizino-[1,2-b]quinoline-10,13(9H,15H)-dione•methanesulfonate was obtained Test 1

A hygroscopicity test was conducted on (lS,9S)-1-amino-9-ethyl-5-fluoro-2,3-dihydro-9-hydroxy-4-methyl-1H,12H-benzo[de]pyrano[3',4':6,7]indolizino[1,2-b]-quinoline-10, 13(9H,15H)-dione•methanesulfonate•dihydrate according to the present invention and (1S,9S)-1-amino-9-ethyl-5-fluoro-2,3-dihydro-9-hydroxy-4-methyl-1H,12H-benzo[de] pyrano[3',4':6,7]indolizino[1,2-b]-quinoline-10,13(9H, 15H)-dione-hydrochloride (control product).

Described specifically, each salt was exposed to high-humidity conditions of 83% and 93% at 25° C. Over a period of 5 days, its weight changes were investigated. The results are shown in FIG. 1.

As can be seen from the results, the control product shows high hygroscopicity and a fast weight change due to hygroscopicity, while the methanesulfonate according to the present invention shows a gradual and small change, although it has hygroscopicity a little.

Incidentally, a color change (yellowish brown—brown; originally: yellow) was observed on a sample of the control product when the sample had been stored at a high relative humidity, thereby suggesting the possibility of decomposition by moisture absorption. The degree of a color change was hence studied by a color difference meter. The control product was stored at a relative humidity of 93% and the degree of a color change was measured. The results are shown in Table 1. In the Table, Lab represents a chromaticity (brightness) and ΔE(H) indicates the degree of a color difference. ΔE(H) of 3, 4 or higher indicates that the color difference is noticeable even to naked eye. Samples of the control product showed a ΔE(H) of 7–8 when stored for a month at 25° C. and 93% relative humidity of 93% and a ΔE(H) of 15–19 when stored for 2 months under the same conditions. It has hence been concluded that the control product decomposes by moisture absorption.

TABLE 1

| Stored for (month) | Color | Lab | ΔE(H) |
|---|---|---|---|
| 0 | Yellow | 81.68–81.69 | — |
| 1 | brown-yellow | 74.96–75.23 | 7.16–7.38 |
| 2 | brown-yellow | 62.65–67.43 | 14.53–19.24 |

No color change, on the other hand, was observed on the methanesulfonate according to the present invention.

What is claimed is:

1. A methanesulfonate salt of a camptothecin compound, said methanesulfonate salt having the formula (1):

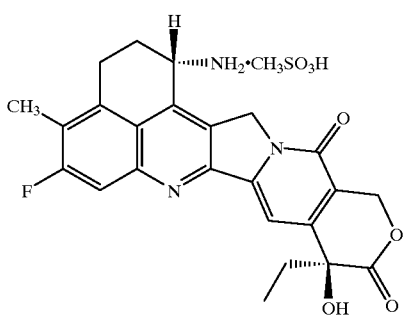

(1)

or a hydrate thereof.

2. A methanesulfonate salt of a camptothecin compound, said methanesulfonate salt having the formula (1):

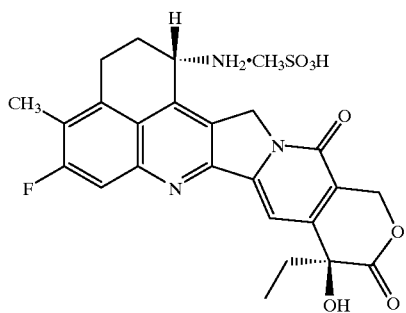

(1)

or a dihydrate thereof.

3. The methanesulfonate salt of claim 1, which is in a form of crystals.

4. A pharmaceutical composition, which consists essentially of:
 a) a methanesulfonate salt of a camptothecin compound as the only active ingredient, the methanesulfonate salt having the formula (1):

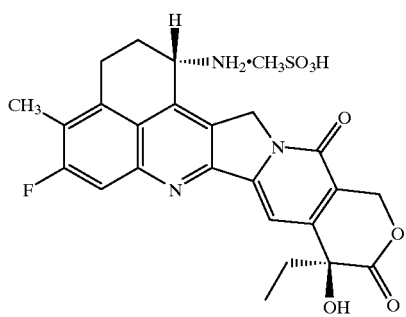

(1)

b) and a pharmaceutically-acceptable carrier.

5. The pharmaceutical composition of claim 4, wherein the methanesulfonate salt is the dihydrate.

6. The methanesulfonate salt of claim 2, wherein the methanesulfonate salt is the dihydrate.

7. The methanesulfonate salt of claim 2, which is in a form of crystals.

* * * * *